United States Patent
Schmidt

(10) Patent No.: US 7,569,513 B2
(45) Date of Patent: Aug. 4, 2009

(54) NICKEL AND COBALT PLATED SPONGE CATALYSTS

(75) Inventor: Stephen Raymond Schmidt, Silver Spring, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

(21) Appl. No.: 12/148,622

(22) Filed: Apr. 21, 2008

(65) Prior Publication Data

US 2008/0194401 A1   Aug. 14, 2008

(51) Int. Cl.
*B01J 23/00* (2006.01)
*B01J 21/00* (2006.01)

(52) U.S. Cl. .................. 502/326; 502/259; 502/260; 502/313; 502/314; 502/315; 502/316; 502/335; 502/337; 502/439; 502/527.24

(58) Field of Classification Search .......... 502/259, 502/260, 325, 337, 313, 314, 315, 316, 326, 502/335, 439, 527.24
See application file for complete search history.

(56) References Cited

U.S. PATENT DOCUMENTS

| | | | |
|---|---|---|---|
| 2,892,801 A | 6/1959 | Sargent | 252/474 |
| 3,036,973 A | 5/1962 | Nathan et al. | 252/474 |
| 3,098,816 A | 7/1963 | Dean et al. | 208/253 |
| 3,129,252 A | 4/1964 | Graham et al. | 260/637 |
| 3,184,417 A | 5/1965 | Hort | 252/474 |
| 3,634,140 A | 1/1972 | Krusenstierna | 136/86 B |
| 3,998,758 A | 12/1976 | Clyde | 252/466 J |
| 4,826,799 A | 5/1989 | Cheng et al. | 502/301 |
| 4,895,994 A | 1/1990 | Cheng et al. | 585/270 |
| 5,536,694 A | 7/1996 | Schuetz et al. | 502/301 |
| 5,627,125 A | 5/1997 | Ebner et al. | 502/331 |
| 6,087,296 A | 7/2000 | Harper | 502/301 |
| 6,156,694 A | 12/2000 | Harper | 502/301 |
| 6,262,307 B1 | 7/2001 | Freund et al. | 564/416 |
| 6,284,703 B1 | 9/2001 | Ostgard et al. | 502/301 |
| 6,309,758 B1 * | 10/2001 | Schmidt | 428/570 |
| 6,376,708 B1 | 4/2002 | Morgenstern et al. | 562/538 |
| 6,391,929 B1 | 5/2002 | Hughes et al. | 518/715 |
| 6,395,403 B2 | 5/2002 | Schmidt | 428/570 |
| 6,414,201 B1 | 7/2002 | Shimazu et al. | 568/863 |
| 6,429,337 B1 | 8/2002 | Schmidt | 564/423 |
| 6,482,315 B1 | 11/2002 | Roberie et al. | 208/249 |
| 6,558,533 B2 | 5/2003 | Schmidt et al. | 208/244 |
| 6,610,628 B2 | 8/2003 | Nordquist et al. | 502/159 |
| 6,706,662 B2 * | 3/2004 | Morgenstern et al. | 502/345 |
| 6,790,996 B2 | 9/2004 | Ansmann et al. | 564/491 |
| 7,329,778 B2 * | 2/2008 | Morgenstern et al. | 562/538 |
| 2002/0019564 A1 * | 2/2002 | Morgenstern et al. | 562/539 |
| 2002/0037808 A1 | 3/2002 | Ostgard et al. | 502/301 |
| 2002/0038051 A1 | 3/2002 | Ostgard et al. | 562/538 |
| 2002/0161259 A1 | 10/2002 | Morgenstern et al. | 562/542 |
| 2003/0019794 A1 | 1/2003 | Schmidt et al. | 208/244 |
| 2004/0137288 A1 * | 7/2004 | Morgenstern | 429/17 |
| 2005/0159305 A1 | 7/2005 | Morgenstern et al. | 502/331 |

FOREIGN PATENT DOCUMENTS

| | | | |
|---|---|---|---|
| DE | 826 134 | 12/1951 | ............ 12/27 |
| DE | 44 12 065 | 10/1995 | |
| GB | 1119512 | 7/1968 | |
| JP | 01126738 | 11/2001 | |
| SU | 1558459 A1 | 4/1990 | |

OTHER PUBLICATIONS

H. Schulz, "Short History and Present Trends of Fischer-Tropsch Synthesis", Applied Catalysts.A, v. 186, pp. 3-12 (1998).
R.J. Farrauto and C.H. Bartholomew, Chapter 9 of "Fundamentals of Industrial Catalytic Processes", pp. 523-535, pub.: Blackie Academia & Professional, 1997.
"Skeleton Catalysts in Organic Chemistry" by B.M. Bogoslawski and S.S. Kaskowa.
"Use of Nickel Skeleton Catalyst in Organic Chemistry" VEB Deutsches Verlag der Wissenschaften, Berlin 1960, p. 40-124.
Zhou X et al.—"Selective Synthesis of N-monoalkyl Aryl-amines from Nitro Aromatic Compounds by Reduction—alkylation" Dyes and Pigments, Elsevier Applied Science Publishers. Barking, GB vol. 36, No. 4 Mar. 16, 1998, pp. 365-371—XP004107990 ISSN:01 43-7208 Abstract.
Hawley's Condensed Chemical Dictionary (Eleventh Edition) Revised by N.Irving Sax and Richard J. Lewis, Sr., p. 240 (1987).

* cited by examiner

*Primary Examiner*—Cam N. Nguyen
(74) *Attorney, Agent, or Firm*—Charles A. Cross

(57) ABSTRACT

Novel nickel and/or cobalt plated sponge based catalysts are disclosed. The catalyst have an activity and/or selectivity comparable to conventional nickel and/or cobalt sponge catalysts, e.g., Raney® nickel or Raney® cobalt catalysts, but require a reduced content of nickel and/or cobalt. Catalysts in accordance with the invention comprise nickel and/or cobalt coated on at least a portion of the surface of a sponge support. Preferably, the sponge support comprises at least one metal other than or different from the metal(s) contained in the coating. The method of preparing the plated catalysts, and the method of using the catalysts in the preparation of organic compounds are also disclosed.

35 Claims, No Drawings

NICKEL AND COBALT PLATED SPONGE CATALYSTS

FIELD OF THE INVENTION

The present invention relates to novel sponge catalysts and to processes for the preparation and use thereof. More specifically, the present invention relates to novel nickel and/or cobalt plated sponge catalysts, the method of preparing the catalysts, and the method of using the catalysts in the preparation of organic compounds.

BACKGROUND OF THE INVENTION

Catalysts based on highly porous nickel materials are well known. Such materials are part of a family of metal alloy derived products sold by W. R. Grace & Co. Conn. under the trademark "Raney®." These porous materials, when microscopically viewed, take on a sponge-like appearance having tortuous pore channels throughout the nickel particle. Thus, such metal alloy materials are generically viewed as sponge products. The sponge catalyst product is normally referred to in terms of the metal which constitutes the major component of the sponge product. These high surface area products have been found to have sites for hydrogen activation and, thus, exhibit catalytic activity when used in the preparation of various organic compounds, such as, for example, the hydrogenation of nitro-substituted organics to their corresponding amine compound.

In general, sponge catalysts, such as porous nickel catalysts are formed by first producing a base metal-aluminum (preferred) or base metal-silicon alloy using conventional metallurgical techniques. The formed alloy is ground into a fine powder and classified by passing it through a sieve to provide a material having a desired particle size, which is normally less than 500 microns and, preferably less than 75 microns. Larger particles are recycled for further grinding.

The alloy powder is then treated with a solution of a base to leach out a substantial amount of the aluminum metal or silicon present. The base may be selected from either an inorganic (preferred) or organic compound. For example, in conventional processes an aqueous solution having from about 5 to 50 weight percent concentration of an alkali metal hydroxide (e.g., sodium hydroxide) is employed as the leaching agent. The treatment of the alloy is usually carried out at elevated temperatures of from about 40° C. to 110° C. The alloy powder can be directly added to the alkali solution or it can be formed into an aqueous suspension, which is then contacted with the alkali solution. The aluminum contained in the alloy dissolves to form an alkali metal aluminate (e.g., sodium aluminate) with vigorous evolution of hydrogen. When silicon is in the alloy, the base forms the corresponding alkali metal silicate. The powder and alkali are normally allowed to remain in contact with each other for several hours at elevated temperature (e.g., 40°-110° C.) until the aluminum (or silicon) content is reduced to the desired level. The crude sponge catalyst is separated from the reaction liquor and then conventionally washed with water until the wash water has a slightly alkaline pH value of about 8. The pore volume, pore size and surface area of the leached alloy will depend upon the amount of aluminum (or silicon) in the initial alloy and the degree of leaching.

The metal alloy used to prepare sponge catalysts is generally composed of a major amount of a base metal selected from nickel, cobalt, copper, iron or mixtures thereof, alloyed with aluminum and minor amounts of additional stabilizing or promoter metals. These additional metals typically include metals such as iron, chromium or molybdenum, as deemed appropriate for a particular application. The concentration of a base metal at the surface of the sponge after leaching will generally be limited by the concentration of the metal introduced at the alloying stage. Consequently, the enhancement of concentration of a particularly active base metal, e.g., nickel and/or cobalt, at the surface of a sponge, requires use of major amounts of these metals at the alloying stage.

A typical Raney® cobalt or nickel catalyst has up to about 95% of the primary metal, i.e., nickel and/or cobalt. With the price of nickel currently averaging over $3.00 per lb. and that of cobalt averaging about $9.00 per lb., the cost of using such catalysts can be prohibitively expensive, especially in reactions involving inexpensive organic reactants and products, such as the conversion of dextrose to sorbitol or the conversion of nitrites to amines, wherein the catalyst price may be considered a significant cost component of the overall process.

It is highly desirable to provide sponge-based catalysts having a catalytic activity comparable to conventional nickel- or cobalt-containing sponge catalysts, e.g., a Raney® nickel or Raney® cobalt, which catalysts have a reduced overall content of nickel and/or cobalt, and a high concentration of these metals at the surface of the catalyst.

SUMMARY OF THE PRESENT INVENTION

The present invention provides novel nickel and/or cobalt containing sponge catalysts, which have an activity and/or selectivity comparable to conventional nickel and/or cobalt sponge catalysts, e.g., Raney® nickel or Raney® cobalt catalysts, but which require a reduced overall content of nickel and/or cobalt. Typically, the catalysts of the invention comprise nickel and/or cobalt coated on at least a portion of the surface of a sponge support. Preferably, the sponge support comprises at least one metal selected from the group consisting of iron, copper, nickel, cobalt or mixtures thereof. Most preferably, the sponge support is a Raney® metal alloy-derived sponge support. The catalysts of the invention offer the economical advantage of increased concentrations of expensive nickel and/or cobalt at the surface of the catalyst relative to the concentration of such costly metals in the sponge support comprising the catalysts.

In a particularly preferred embodiment of the present invention, composite sponge catalysts in accordance with the invention comprise a sponge support coated with nickel and/or cobalt wherein the sponge support comprises at least one metal other than or different from the metal(s) contained in the coating, e.g., as with a nickel sponge support having a cobalt coating deposited thereon. Preferably, the sponge support comprises at least 50 weight percent of a metal, which is different from the metal(s) contained in the coating. Such a composition offers the advantage of efficient and versatile use of metals in the coating and support to create catalysts having unique characteristics of catalytic activity and/or selectivity associated with a mixture of metals.

Advantageously, the present invention provides nickel and/or cobalt containing sponge catalysts having a reduced overall content of nickel and/or cobalt as compared to conventional nickel and/or cobalt containing sponge catalysts, e.g., Raney® nickel or Raney® cobalt catalysts, while having a high concentration of nickel and/or cobalt metal at the surface of the catalysts.

The present invention further provides novel nickel and/or cobalt sponge catalysts having a sponge support and a nickel and/or cobalt containing coating having different characteristics of selectivity and catalytic activity.

The present invention also provides nickel and/or cobalt plated sponge catalysts having a nickel and/or cobalt concentration at the surface of the catalyst which is increased relative to the concentration of nickel and/or cobalt contained in the sponge support comprising the catalyst.

The present invention further provides a method of preparing the nickel and/or cobalt plated catalysts of the invention.

The present invention also provides improved processes for the preparation of organic compounds using the nickel and/or cobalt containing catalysts of the invention.

These and other aspects of the present invention are described in further detail below.

DETAILED DESCRIPTION OF THE INVENTION

For purposes of this invention, the term "sponge support" is used herein to mean a porous material which is comprised of metal(s) and has a high surface area. Surface area can be defined as the total area (two dimensional measurement in square meters) of exposed surface of a solid material whether in the form of fibers, particles, sponges, and the like. This area includes those areas that are contained in irregularities, cracks and openings of all type, internal and external to the outermost boundary of the material. The term "porous" is used herein to describe that portion of the surface internal to the solid structure of the material. It is within the scope of this definition that the porosity may take the form of tortuous pores extending throughout the volume of the material. The porous metal materials typically have a pore volume (nitrogen BET) of at least about 0.05 cc/g; an average pore diameter of at least 20 Angstroms; and a surface area (BET) of at least 5 $m^2$/g, preferably at least 10 $m^2$/g. The porous metal material may be a Raney® metal alloy-derived sponge material or a sponge material made by other conventional methods sufficient to achieve the required characteristics of porosity and high surface area, e.g., reduction of metal oxides or ores (e.g., iron sponge made by the 'direct reduction of iron' process, available from Reade Advanced Materials, Providence, R.I., or 'carbonyl iron' powders available from BASF Aktiengeselloschaft, Germany). Where the porous material is a Raney® metal alloy-derived sponge material, the material may also include residual aluminum in the form of a solid solution with metals, e.g., iron, nickel and the like, metal aluminide or hydrous aluminum oxide.

The term "metal(s)" is used herein to mean a chemical element that in its pure form would exist in a condensed state of matter at standard conditions (atmospheric pressure and room temperature), that typically forms positive ions when in solution (e.g. acidic solution), and whose oxides typically form hydroxides rather than acids when in contact with water. Specific examples of metals include, but are not limited to, the elements of the transition series of the Periodic Table (both base metals, e.g., iron, copper, nickel, cobalt, molybdenum, chromium, zinc, manganese, etc., and precious metals, e.g., palladium, platinum, etc.), plus main group elements from group IA (e.g., sodium), group IIA (e.g., magnesium), and group IIIB (e.g., aluminum). An element which is a metal may occur in more than one species, i.e. in the "metallic form, the fully reduced or zero valent form (e.g. $Ni^°$, also known as "nickel metal"), a component of a metal-containing compound, examples of which may include, but are not limited to, oxides, hydroxides, carbonates, sulfates, chlorides, phosphides, borides, aluminides, and the like, or a "partly metallic" form (i.e. containing both the zero valent form and compounds of the metal). It is within the scope of this definition that the compound may be an oxidized form of the metal (e.g. NiO or $Ni(OH)_2$). The metal-containing compounds may also include a solid solution such as, for example, aluminum dissolved in metals such as iron, nickel, cobalt and the like. The terms "nickel", "cobalt", "iron", "copper", "chromium" and the like, as used herein refer to the metal irrespective of its form (metallic, oxidized or contained in another compound), unless otherwise specified. Stated percentages of metals in compositions recited herein are on a "metals-only basis".

For purposes of this invention, the deposition process may be hereinafter referred to, interchangeably, as "depositing", "plating", "coating", or "dispersing" the nickel and/or cobalt metal(s) onto the surface of the sponge support.

The catalyst of the invention is comprised of a sponge support having at least a portion of its surface coated with a metal selected from the group consisting of nickel, cobalt and mixtures thereof. In accordance with one embodiment of the invention, the sponge support comprises at least one metal other than or different from metal(s) contained in the coating. For example, when the coating on the support comprises nickel, the sponge support comprises at least one non-nickel metal, such as, for example, iron, copper, cobalt, aluminum and mixtures thereof. Where the coating on the support comprises cobalt, the sponge support comprises at least one non-cobalt metal, such as, for example, iron, copper, nickel, aluminum and mixtures thereof. Preferably, the sponge support comprises at least 50 weight percent, most preferably at least 60 weight percent, even more preferably at least 80 weight percent, of a metal other than or different from the metal(s) contained in the coating.

The composition of the invention catalyst may be defined in terms of its total nickel and/or cobalt content. The total nickel and/or cobalt content depends on the amount of nickel and/or cobalt initially present in the sponge support, the amount of nickel and/or cobalt deposited during the plating process, and the amount of weight loss, i.e. by displacement or dissolution of metals from the support, by the sponge support during the plating process. The loss of metals during plating are generally limited mainly to the non-Ni and non-Co metal parts of the sponge support, which may be chemically removed at low to moderate levels (e.g., less than 20% of the original sponge support weight). In combination with the nickel and/or cobalt present in the sponge support and subsequently deposited during plating, these losses affect the final (total) nickel or cobalt content of the plated sponge catalyst.

For example, if a sponge support contains 20% Ni before the addition of Ni at 30% of the original sponge support weight (and assuming 100% transfer of Ni from solution to sponge support, and 10% loss of weight from the sponge support during deposition), the final material's % Ni is= (20%+30%)/(1.00+0.30−0.10)=about 42%. The additive and subtractive terms in the denominator of this expression accomplish the re-normalization of the total solid material weight. The material balance calculation is completed by verifying that the non-Ni part of the final material is=(80%− 10%)/(1.00+0.30−0.10)=about 58%.

Typically, the plated sponge catalyst of the invention comprises less than 98, preferably less than 80, more preferably less than 60, and most preferably less than 30, weight percent of nickel and/or cobalt in the total catalyst composition. In a particularly preferred embodiment of the invention, plated catalysts in accordance with the invention comprise from about 8 to about 98, preferably from about 10 to about 60, most preferably from about 15 to about 45, weight percent of nickel and/or cobalt in the total catalyst composition.

Nickel and/or cobalt coated sponge catalysts of the invention have a nickel and/or cobalt concentration at the catalyst surface, i.e., the outermost 50 Å of the catalyst as determined by X-ray Photoelectron Spectroscopy (XPS) or Electron Spectroscopy for Chemical Analysis (ESCA), which is increased relative to the concentration of nickel and/or cobalt contained in the sponge support comprising the catalyst. For example, where the sponge support is an iron sponge containing minor amounts of nickel, the nickel concentration at the surface of the coated catalyst is increased relative to the concentration of nickel contained in the sponge support. Typically, the atomic ratio of the concentration of nickel and/or cobalt to the concentration of at least one other metal contained in the support, e.g., iron, at the surface of the invention catalyst as measured by XPS or ESCA, is 0.20 or greater, preferably 0.5 or greater, most preferably 1.0 or greater, as compared to less than 0.10 for an uncoated sponge support. Further, where the support is a Raney® nickel containing residual aluminum, the nickel concentration at the surface of the coated Raney® nickel catalyst is increased relative to the concentration of nickel contained in the Raney® nickel support. Similarly, cobalt can be coated on a Raney® cobalt sponge support to enhance cobalt concentration at the surface of the support.

Sponge supports useful in the catalysts of the invention include any conventional sponge materials. As will be understood by one skilled in the art, the amount of each metal present in the sponge support will vary, depending on such factors as the intended use of the final catalyst, the desired catalytic performance, cost constraints, etc. In a preferred embodiment of the invention, the sponge support comprises at least 50, more preferably at least 60, and most preferably at least 80, weight percent of metals selected from the group consisting of iron, copper, nickel, cobalt or mixtures thereof. The amount of nickel and/or cobalt in the sponge support will be less than 98, preferably less than 40, and most preferably less than 30, weight percent of the support. Typically, the amount of nickel and/or cobalt present in the support ranges from about 0 to about 98, preferably from about 2 to about 40, and most preferably from about 5 to about 30, weight percent of the support.

It is also within the scope of this invention that minor amounts (e.g., less than 40 weight percent, preferably less than about 30 weight percent, most preferably less than 15 weight percent) of additional stabilizing or auxiliary metals may be included in the support. Such additional metals may include, but are not limited to, metals selected from the group consisting of copper, iron, chromium, titanium, tungsten, molybdenum, zinc, zirconium, manganese, aluminum, vanadium and mixtures thereof. Typically these additional metals are present in the support in amounts ranging from about 40 to about 1, preferably from about 30 to about 2, most preferably from about 15 to about 3, weight percent of the sponge support.

The sponge support may also contain a precious metal dopant selected from the group consisting of platinum, palladium, iridium, rhodium, osmium, ruthenium, rhenium and mixtures thereof, as described in U.S. Pat. Nos. 6,309,758 and 6,395,403, said references being herein incorporated in their entirety by reference. Typically the amount of the precious metal dopant present in the support is less than 1.5, preferably less than 1.0, most preferably less than 0.5, weight percent of the support. In a preferred embodiment of the invention the precious metal dopant is present in the support in an amount ranging from about 1.5 to about 0.1, preferably from about 1.0 to about 0.5, most preferably from about 0.5 to about 0.1, weight percent of the support.

The sponge support will typically have a pore volume (nitrogen—BET) ranging from about 0.05 to about 0.3 cc/g, preferably from about 0.1 to about 0.2 cc/g, and an average pore diameter ranging from about 10 to about 500, preferably from about 40 to about 200, Angstroms. The surface area (BET) of the sponge support is at least 5 $m^2/g$, preferably at least 10 $m^2/g$. In one embodiment of the invention, the surface area of the sponge support ranges from about 10 to 200, preferably from about 20 to about 150 $m^2/g$. The sponge support may be in any form having a measurable BET surface area, e.g. particles, monoliths, grids, fibers, plates, and the like. Preferably the support is in the form of particles. When used as particles, the median particle diameter of the sponge support is typically less than 500 microns, preferably less than 75 microns. When contemplated for use in fixed bed reactions, the median particle diameter of the sponge support ranges from about 0.1 to about 0.8 cm, preferably from about 0.15 to about 0.5 cm.

In a preferred embodiment of the invention, the sponge support is a metal alloy derived sponge (e.g. a Raney® metal sponge), typically formed by partial and selective extraction (or "leaching", "digestion") of aluminum and/or silicon from an alloy comprised of aluminum and/or silicon and at least one other metal such as iron. The precursor to the sponge support is an alloy with an extractable component, namely aluminum or silicon. Suitable alloys include, but are not limited to, metal-aluminum alloys wherein the metal is selected from the group consisting of iron, steel, copper, nickel, cobalt or mixtures thereof. For example, an iron-aluminum alloy is formed by a pyrometallurgical (high temperature melting of metals) process yielding a composition having from about 30 to about 70 weight percent (preferably from about 40 to 60 weight percent) aluminum with the remainder consisting mainly of iron. Smaller amounts of other base metals may, optionally, be present as stabilizers for the sponge support and/or finished catalyst, during and after the formation process. Such stabilizers may include, but are not limited to, a metal selected from the group consisting of nickel, copper, cobalt, chromium, molybdenum, tungsten, manganese, titanium, zirconium, vanadium or zinc, in various combinations, of up to about 20 percent, preferably less than 15 percent, percent by weight of the alloy composition.

When the catalyst is intended for use in a fluidized or "slurry" type reactor, the alloy is formed into a powder typically by crushing and grinding, but alternatively by atomization (i.e., droplet formation from the molten stage), into particles having an median particle size of less than 500 micron diameter, preferably less than 75 micron diameter. The alloy powder is converted to a higher surface area form or "activated" by leaching (extracting) the aluminum from the alloy with an aqueous alkali solution, such as an aqueous solution of sodium hydroxide or potassium hydroxide. The alkali is used at concentrations of at least about 15 weight percent, preferably from about 15 to about 35 weight percent, and most preferably from about 20 to about 30 weight percent, of the solution. The leaching is carried out at temperatures ranging from ambient temperature to elevated temperatures up to the boiling point of the leaching solution. Temperatures of from about 40° C. to 110° C. (preferably 60° C. to 100° C.) are typical to cause substantial rate of leaching and removal of the aluminum from the alloy.

When the present catalyst is contemplated for use in fixed bed (e.g. packed column type) reactors, the sponge support preferably has a median particle size diameter (or largest dimension) of from about 0.1 to about 0.8 cm. This is achieved either by crushing and size-classifying (e.g., sieving) the original alloy, or by forming aggregate bodies by binding finer powder into regular shapes, by extrusion or pelletizing and heat treatment. (See U.S. Pat. Nos. 4,826,799 and 4,895,994, which patents are herein incorporated in their entirety by reference). The alloy particles or formed particles are leached with an aqueous alkali solution as described above having an alkali concentration of from about 5 to 35 weight percent, preferably from about 10 to about 25 weight percent of the solution. The leaching is normally carried out at elevated temperatures of from about 30° C. to about 90° C., preferably from about 30° to about 50° C. in the case of crushed alloy particles, and preferably from about 60° to about 90° C. in the case of previously heat-treated formed particles. After being leached, sponge support is washed with water to remove the aluminate by-product. Total removal of the aluminate is not required. However, washing is preferably continued until the effluent wash water has an alkaline pH of from at least 7 to about 12. The washing is conducted with water (or a dilute aqueous solution at modified pH) having a temperature ranging from ambient to about 60° C., preferably from about 30° C. to about 45° C. It is preferred that the washing be conducted under an inert (e.g., $N_2$ or Ar) atmosphere or one having a dilute concentration (2-8%, preferably 3-5%) of hydrogen carried in an inert gas. The method for washing can either be batch type (discontinuous process also sometimes known as 'decantation', using cyclic addition of a fixed amount of washing liquid followed by agitation, separation of solids from liquid, followed by addition of more liquid as the cycle repeats), or continuous, appropriate for fixed bed catalysts, in which flowing liquid is simultaneously being both introduced and removed.

Plating Process

The catalysts of the invention are prepared by depositing a nickel and/or cobalt coating onto at least a portion of the surface of a sponge support. The present invention shall hereafter be described, by way of example, by the deposition of nickel onto a sponge support made by the Raney® process, wherein the support contains at least 50 weight percent iron. It is understood however, that the process as generally describe hereafter is also be effective to coat cobalt, alone or in combination with nickel, onto a variety of sponge supports.

Before and during the plating process, it is understood that the sponge support is protected from air by, for example, keeping it immersed in an aqueous solution, preferably the residual wash solution obtained during preparation of the support as described herein above, and maintaining it under a non-oxidizing atmosphere (noble gas or $N_2$), and/or sparging a suspension containing the support with a non-oxidizing gas. Hydrogen gas itself, if introduced as fine bubbles and with sufficiently vigorous mixing, is also a useful agent in this process, but primarily to help maintain a non-oxidizing environment throughout the process by exclusion of air.

Further, it is to be understood that the deposition process is conducted in a vessel capable of being heated and stirred while being protected against air introduction and evaporative losses of liquid. The contents of the vessel are being stirred (or in the case of a fixed bed catalyst, the liquid phase is optionally circulated with respect to the stationary solid phase by pumping) throughout the duration of the process unless otherwise stated.

The nickel coating may be deposited onto the sponge support using an aqueous plating slurry formed by a mixture of an aqueous slurry containing the support and a suitable nickel salt. The aqueous slurry containing the support is formed from a mixture of water or an aqueous solution with the sponge support. Where the support is a Raney® metal alloy derived sponge, the support containing slurry may exist after the leaching and washing steps involved in making the sponge by simply leaving the sponge in water (optionally adding more water) to protect it from air. Alternatively, the support containing slurry may be formed using a sponge support that is stable in air by placing said support into water or an aqueous solution.

The concentration of the sponge support in the aqueous slurry will generally range from about 2 to about 15 weight percent of the slurry. Preferably, the concentration of the sponge support in the slurry will range from about 3 to about 12 weight percent of the slurry, with a range of from about 5 to about 10 weight percent being the most preferred.

Prior to the addition of nickel salt to the aqueous slurry containing the sponge support, the pH of the slurry may optionally be adjusted to more closely match the final pH of the plating slurry, e.g., pH ranging from about 5.0 to about 6.0, and/or to remove surface iron oxide(s) or other metal oxides formed in the leaching and washing steps described above in order to form a support surface more receptive to nickel deposition. This can be achieved by the addition of a suitable acid to the slurry. For example, sulfuric acid may be added in an amount sufficient to achieve a pH in the range of about 5.5 to about 6.0 prior to adding nickel sulfate to the slurry. The amount and type of acid added will vary depending on the pH resulting from the prior washing steps, and on the stability of the support at acid pH. To remove surface oxides, oxalic acid or acetic acid, for example, may be used, optionally at elevated temperature, e.g., about 30° to 60° C., to provide for more effective nickel plating.

The nickel salt may be added to the sponge support containing aqueous slurry as a dry powder, or, preferably, dissolved in an aqueous solution. When adding the nickel salt, the slurry preferably is stirred at a rate sufficient to keep the support particles suspended. The nickel salt may be added to the slurry all at once or gradually.

The concentration of the nickel salt used will vary depending upon the desired catalytic activity and the intended catalytic process. Generally, the concentration of nickel salt in the plating slurry will be that concentration sufficient to provide a catalytically effective amount of nickel on the surface of the sponge support. Typically, the concentration of nickel salt in the plating slurry is that concentration sufficient to provide at least 10 weight percent, preferably greater than about 15 weight percent, of nickel relative to the initial weight of the sponge support in the slurry.

Nickel salts useful to prepare the catalyst of the invention will vary depending upon such factors as cost constraints, solubility in the plating solution, and effectiveness for the intended catalytic application (as based on purity requirements and types of anions present). In general, however, commonly available acid salts of nickel will be useful provided that anions introduced by the chosen salt do not cause deactivation or self-fouling of the resulting metal surfaces and can be sufficiently washed out of the newly-plated catalyst to provide the required catalytic performance. The later-described final washing steps can be varied in combination with the metal salt choice to affect this, as an iterative improvement based on performance. Typically, nickel salts will include, but are not limited to, sulfate, chloride, nitrate, acetate, citrate and the like.

A reducing agent is added to the plating slurry to reduce nickel ions in solution to nickel. The choice of reducing agent can be partly based on whether the electrode potential associated with its half-reaction is large enough to offset the electrode potential for the half-reaction of ions being reduced to plated metal. In the case of depositing nickel this would theoretically direct one to use reducing agents with half-reactions of greater than about +0.26. In actual practice it is not always possible to use previously-measured electrode potentials to predict suitability of a given reducing agent for use in this invention, because the conditions of use here may vary from those used in the previous measurements. In particular the pH of the plating slurry may alter the effectiveness of reducing agents, depending on whether they are more compatible in solution with acids or bases, and depending on the extent to which the redox equilibrium produces or consumes the non-neutral species $H^+$ or $OH^-$. Typically, the pH of the plating slurry useful to prepare the catalyst of the invention is acidic, i.e. less than 7, preferably less than 6.

Examples of useful reducing agents include, but are not limited to, salts of formic acid (HCOOH), e.g., sodium formate; salts of other carboxylic acids, such as oxalic, gluconic, pyruvic, and glyoxilic; carboxylic acids; low molecular weight (e.g. 6 carbon atoms or less) aldehydes; reducing sugars such as glucose, hypophosphite ($NaH_2PO_2$); borohydride ($NaBH_4$); aminoboranes such as DMAB; lithium aluminum hydride ($LiAlH_4$); hydrazine ($H_2N-NH_2$); and low molecular weight alcohols such as isopropanol and mixtures thereof. Preferred reducing agents include, but are not limited to, formaldehyde (HCHO), sodium hyposphosphite, sodium formate, gluconate, oxalate, sodium borohydride and mixtures thereof. At low pH conditions, the actual species present may include acid forms of some reagents in addition to the anionic form, such as hypophosphorous acid, e.g., in addition to the hypophosphite ion. These acids, rather than their neutralized salt forms, may be added to the plating mixture if a pH effective for plating can be achieved. This allows for the option of fewer reagents and possibly fewer steps in the plating process, if other acids used for pH adjustments are omitted.

The reducing agent may be added following addition of the metal salt, or optionally during the chemical and thermal initiation of the plating process. The reducing agent may be added all at once or gradually over time to initiate and control the plating process. Generally, the reducing agent is used in an amount, as readily determined by the skilled artisan, sufficient to accomplish the desired catalytic performance. Typically, the reducing agent is added in an amount of at least the stoichiometric amount necessary for the redox reaction with the metal ions, e.g., nickel ions, in solution, but it could be used in excess up to a multiple of several molar equivalents.

If, during the deposition process, the nickel is deposited at a rate which tends to unevenly coat the support, a more even coating may often be obtained by including a complexing or chelating agent in the nickel salt solution to control (i.e., slow) the rate of nickel deposition and obtain a more even coating. A chelating agent may also be beneficial to inhibit any displaced metal ions from re-depositing onto the sponge support. Suitable chelating agents include, for example, hydroxy carboxylic acids (e.g., lactic acid, maleic acid, citric acid, gluconic acid and tartaric acid) and salts thereof (e.g. sodium potassium tartrate, also described in the art as "Rochelle salt"), with citric and gluconic acids and salts thereof being particularly preferred. Typically, the chelating agent is added in an amount of at least the stoichiometric amount necessary for the complexation reaction with the metal ions, e.g., nickel ions, in solution, but it could be used in excess up to a multiple of several molar equivalents.

It is also within the scope of the invention to optionally add one or more metal stabilizers to the plating slurry. Suitable metal stabilizers include, but are not limited to, salts or complexes of metals selected from the group consisting of chromium, titanium, niobium, tantalum, zirconium, vanadium, molybdenum, manganese, tungsten, bismuth, and mixtures thereof. The presence of such stabilizers tends to extend the life of the catalyst during use, i.e., increase the number of reaction runs in which the catalyst can be used before its activity decreases to unacceptable levels, or increase the shelf life of the catalyst prior to use. The amount of metal stabilizers can vary within wide limits depending on desired results. Preferably, however, the total concentration of metal stabilizers is less than 10% of the total catalyst composition. More preferably, the total concentration of the metal stabilizers is less than 5%.

Prior to initiation of the plating process, the plating slurry will preferably have a pH within a range that is constrained at its lower end by the beginning of solubility of the sponge support in the plating slurry, and at its upper end by the beginning of the precipitation of nickel as particles separate from and/or unattached to the support. Typically the pH should be greater than 4.0. Preferably, the pH should range from about 5.0 to about 7.0 depending on such factors as the presence of chelating or complexing agents and the solubility of the sponge support. Most preferably, the pH at this stage will be that pH which naturally occurs upon contact of the nickel salt with the support and reducing agent without chelating agents present, i.e., from about 5 to about 6. As will be understood by one skilled in the art, the pH of the plating slurry can be adjusted by the addition of minor amounts of base or acid as needed.

Further, prior to initiation of the deposition process, the plating slurry is mixed with agitation for a time sufficient, e.g., about 5 to about 10 minutes, to ensure uniform distribution of reagents in the slurry.

The nickel coating may be deposited on the sponge support using various techniques well known in the art for depositing metal onto metal surfaces. These techniques include, for example, liquid phase methods, such as electrochemical displacement plating and electroless plating. A particular preferred technique of acidic electroless plating, optionally in combination with electrochemical displacement plating, is described below.

Electroless plating comprises reducing metal ions to metallic or partly metallic form in a solution in contact with a support wherein all or substantially all of the metal ions reduction is accomplished by an external reducing agent rather than the support itself. In the present invention, electroless plating of the nickel coating on the support is accomplished by adjusting the pH and temperature to ranges where the reducing agent is effective to deposit all or substantially all of the nickel metal onto the support. Electroless plating may be accomplished by adjusting the pH of the aqueous plating slurry to about 5.5 to about 7, preferably about 5.5 to about 6.0, by the addition of aqueous acid (such as acetic or sulfuric acid) or base (such as sodium hydroxide or ammonia), and subsequently, adjusting the temperature of the slurry to at least 30° C. Preferably, the temperature is adjusted to be within a range of about 50° C. to about 90° C.; most preferably the temperature is adjusted to within a range of about 60° C. to about 85° C.

It is also contemplated that the plating process may optionally be accomplished hydrothermally, i.e., under applied pressure to achieve a temperature of greater than 100° C.

Where the metals of the sponge support are less stable, i.e., more easily oxidized under the plating reaction conditions than the metals in the coating, electrochemical displacement plating may optionally be first used to initiate the deposition process, followed by electroless plating as herein described above to complete the deposition. Like electroless plating, displacement plating involves reducing metal ions in solution to metal. However, unlike electroless plating, in electrochemical displacement plating, substantially all the metal ions reduction which occurs is accomplished by metals of the support. In the present invention, the electrochemical displacement plating process may be accomplished by adjusting the pH of the plating slurry to about 5 (by addition of a small amount of acid, such as acetic or sulfuric acid), and maintaining such a pH for a time sufficient to initiate the displacement of support metal, e.g., iron, with deposition of nickel from the plating slurry. Typically, the pH is maintained at this level from about 5 to about 10 minutes.

The amount of time for completion of the plating process will vary depending upon such factors as the temperature, pH and type of support. Generally, the plating process proceeds for an amount of time sufficient to effect deposition of all or substantially all of the nickel in the plating slurry on the support surface. In a preferred embodiment of the invention, the plating process is conducted for a time sufficient to provide a nickel coating comprising from about 10 to about 60 grams, preferably from about 15 to about 50 grams, even more preferably from about 20 to about 45 grams, of nickel per 100 grams of the sponge support. Typically, the plating time ranges from about 20 minutes to about 2 hours.

At relatively high loadings of nickel (i.e., greater than about 25 weight percent of the support), it is preferable to apply the metal-containing coating in multiple plating operations. Preferably, the multiple coating is applied in successive plating operations. Further, maintaining high porosity in the product and removal of byproduct salts and residues may be aided by using two or more separate plating operations at lower metal concentrations, separated by washing steps.

For example, a nickel loading in a first plating process ranging from about 5 to about 20 weight percent relative to the sponge support weight, followed by a nickel loading in a second plating operation ranging from about 5 to about 20 weight percent relative to the weight of the sponge support, may be used to provide a combined nickel content of from about 10 to about 40 weight percent nickel on the surface of the sponge support. In between successive plating operations, the agitation of the plating slurry is preferably discontinued and support particles are separated from spent plating solution using a conventional solid-liquid separation process, e.g., filtration or settling. Solids resulting from a prior plating process are preferably washed as described herein above for the preparation of the support, either with water or dilute aqueous solutions of base or acid depending upon the residues to be removed, optionally at elevated temperature, e.g., from about 40° C. to about 60° C. The dilute aqueous solutions of base or acid for washings may be chosen for their effectiveness in removing particular types of residues, e.g., they may contain ions capable of displacing or removing targeted residues: alkali metal hydroxides being capable of displacing $H^+$ ions; chelating anions such as oxalate, citrate, etc. being capable of removing metal cations. Subsequent plating processes are achieved essentially by repeating the above described steps, including addition of nickel salt and other reagents, or optionally pre-treatment with acid prior to plating. All of the optional process variations described hereinabove may be varied as desired in the subsequent plating procedure.

Following completion of deposition, the nickel coated porous sponge catalyst is removed from the spent plating slurry by conventional solid-liquid separation process, e.g., filtration or settling, and is thereafter washed, with water or optionally an aqueous alkaline solution (e.g., NaOH), for a time and at a temperature sufficient to neutralize and/or remove substantially all acid residues and salts.

The washed nickel coated sponge catalyst may be treated at this point to add a metal promoter followed by washing as described above. Suitable metal promoters, include, but are not limited to, metals selected from the group consisting of chromium, molybdenum, titanium, zinc, vanadium, zirconium, or mixtures thereof. The metal promoters may be deposited on the surface of the catalyst in the form of a metal in its zero valent state or in an oxidized state. The promoters may be present in amounts up to 3.0, preferably up to 2.5, most preferably up to 2.0, weight percent of the catalyst. Preferably, the promoter is present in the catalyst in the range of from about 0.2 to about 3, most preferably from about 0.3 to about 2, even more preferably from about 0.5 to about 1, weight percent based on the weight of the catalyst. The promoter metals may be added by conventional processes using a metal salt solution (e.g., Mo can be added using a molybdate salt, or Cr using a chromate salt).

The promoted or unpromoted plated catalyst may also be doped with a precious metal dopant selected from the group consisting of platinum, palladium, iridium, rhodium, osmium, ruthenium, rhenium and mixtures thereof as described in U.S. Pat. Nos. 6,309,758 and 6,395,403, said references being herein incorporated in their entirety by reference, followed by washing as described above. Typically the amount of the precious metal dopant present in the catalyst is less than 1.5, preferably less than 1.0, most preferably less than 0.5, weight percent of the catalyst. In a preferred embodiment of the invention the precious metal dopant is present in the catalyst in an amount ranging from about 1.5 to about 0.1, preferably from about 1.0 to about 0.1, most preferably from about 0.5 to about 0.1, weight percent of the catalyst.

The final catalyst is normally stored as an aqueous slurry until use. Following washing, the plated catalyst can optionally be separated from the final wash solution and stored in an alcohol (e.g. C1-C3 alkanol) or water-alcohol medium.

Composite sponge catalysts of the invention uniquely provide on the surface of a sponge support a nickel and/or cobalt coating having a different catalytic characteristic from the metals comprising the support, e.g., a nickel-based sponge support having a cobalt coating deposited thereon. The ability to provide such a variation in the support and coating enables the efficient and versatile use of metals in the coating and the sponge support to create composite catalysts having the unique properties associated with a mixture of metals. For example, a catalyst having the selectivity and activity characteristics of both nickel and copper may be prepared by depositing nickel onto a copper containing sponge support.

Plated porous base metal catalysts of the invention are useful in the preparation of organic compounds from corresponding precursor organic compounds using catalyzed chemical processes such as hydrogenations, dehydrogenations, reductive alkylations, aminations, and organic coupling reactions. Thus, in general, the plated catalysts of the invention are useful in processes commonly catalyzed by sponge metal catalysts such as Raney®Ni and Raney®Co, or Ni or Co catalysts in which the active metals are supported on conventional metal oxide supports (e.g., Ni/silica or Co/alumina). It is further contemplated that composite catalysts of the invention, e.g., cobalt coated iron based sponge catalysts, are useful to catalyze Fischer-Tropsch synthesis in which CO is reacted with hydrogen to make hydrocarbons, as described in H. Schulz, "Short History and Present Trends of Fischer-Tropsch Synthesis", *Applied Catalysts. A*, v. 186, pp. 3-12 (1998). Other compositions such as highly Mo-promoted modifications of Co/Fe and Ni/Fe may be useful in hydrotreating applications to remove sulfur, nitrogen and phosphorus compounds and heavy metals from petroleum feedstocks prior to further processing the feedstocks into useful fuels, as described in R. J. Farrauto and C. H. Bartholomew, Chapter 9 of Fundamentals of Industrial Catalytic Processes, pp. 523-535, pub: Blackie Academic & Professional, 1997. The novel materials of this invention may also have utility in other applications where hydrogenation catalysts are used with a benefit of reduced costs for the user, e.g., a method for the adsorptive removal of sulfur from hydrocarbons as described in U.S. Ser. No. 09/833,602, filed Apr. 13, 2000, Schmidt, et al., and a method for the preparation of electrode components in fuel cells or hydrogen generators as described in Japanese Patent Application No. 01126738, and U.S. Pat. No. 3,634,140.

In a preferred embodiment of the invention, the plated catalysts of the invention are useful to accomplish more economical catalytic hydrogenation processes when compared to hydrogenation processes carried out using conventional porous sponge catalysts, such as, for example, a Raney®nickel catalyst. Examples of such reactions are described in Skeleton Catalysts in Organic Chemistry by B. M. Bogoslawski and S. S. Kaskowa and in Use of Nickel Skeleton Catalyst in Organic Chemistry VEB Deutsches Verlag der Wissenschaften, Berlin 1960, pg. 40-124, the teachings of which are incorporated herein in their entirety by reference. In particularly, the invention catalysts are useful in a hydrogenation reaction wherein the sugar dextrose, an "aldose" (containing the unsaturated aldehyde group) is the feedstock that is converted to sorbitol, a sugar alcohol useful as a food additive and as an intermediate in pharmaceutical synthesis. As an optional feature of the various catalyzed chemical processes in which catalysts of the invention may be used, further reduction of the coated nickel or cobalt may be practiced as needed. This further reduction may be achieved either prior to adding the catalyst to the catalytic process reactor, e.g., by treatment with hydrogen gas or a chemical reducing agent solution, or preferably in a hydrogenation process may be achieved under applied hydrogen pressure "in situ" prior to or during the early stages of the process.

The final catalyst may also contain trace amounts of phosphides, borides, carbonates, and the like, as compounds of the plated nickel and/or cobalt, or similar residues incorporated during the plating process, depending on the type and degree of decomposition of the reducing agents employed during the deposition process. This may in turn affect the suitability of the resulting material for specific catalytic applications such as the hydrogenation of certain types of organic compounds (e.g., nitrites when hydrogenated to amines).

To further illustrate the present invention and the advantages thereof, the following specific examples are given. The examples are given as specific illustrations of the claimed invention. It should be understood, however, that the invention is not limited to the specific details set forth in the examples.

All parts and percentages in the examples, as well as the remainder of the specification, which refers to solid compositions or concentrations, are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Analytical and performance parameters recited in the Examples are defined as follows:

The average surface concentration of a deposited metal was compared to the average surface concentration of a metal contained in support, and expressed as an atomic ratio, e.g., Ni/Fe in a nickel coated sponge iron support. Ni/Fe and other atomic ratio values as recited in the Examples were determined using XPS or ESCA methods as described in U.S. Pat. Nos. 6,395,403 and 6,309,758, within a surface depth of the outermost 50 Å of a catalyst material and are an average of ratios catalyst particles measured simultaneously.

Productivity values as recited in the Examples were determined by the rate at which dextrose was converted to sorbitol using a given amount of catalyst. One defined measure of productivity, which is the amount of a given product made per unit time per unit weight of catalyst in a batch process run to complete conversion of feedstock to product, was calculated as follows:

$$\text{Productivity} = \frac{\text{Weight Product}}{(\text{Batch completion time})(\text{Weight catalyst})}$$

When the operating conditions of the batch test are fixed (i.e., weight of feedstock, temperature, and pressure, plus weight of catalyst or 'catalyst loading' are all held fixed), a series of catalysts tested at these conditions can be compared in productivity by the simple ratio of their batch completion times. For example, for any given experimental catalyst relative to the catalyst designated as the 'standard', productivity may be calculated as follows:

$$\text{Productivity ratio} = \frac{\text{Productivity (experimental)}}{\text{Productivity (standard)}} = \frac{\text{Batch }compl.\text{ time (standard)}}{\text{Batch }compl.\text{ time (experimental)}}$$

The productivity ratio can be refined to allow for comparison of catalysts having very different active metal contents. This method includes cost efficiency in the evaluation, since (as is the case here with Ni or Co) the active metal component may also be the most expensive metal among the raw materials (based on cost multiplied by total amount used). If the total weight of catalyst is still fixed, but the active metal content (Ni, in this example) differs between the experimental and standard catalysts), the productivity ratio may be calculated as:

$$\frac{\text{Productivity (experimental)}}{\text{Productivity (standard)}} = \frac{[\text{Batch }compl.\text{ Time }(std)] \times [\text{Ni content }(std)]}{[\text{Batch }compl.\text{ Time }(exp)] \times [\text{Ni content }(exp)]}$$

This ratio based on Ni content only becomes a relevant discriminator for ranking the value of catalysts with comparable (relatively short) absolute batch times. The first requirement of the catalyst is usually that it perform adequately, and a secondary requirement is cost (proportional to Ni content). Thus, e.g., if an experimental catalyst with 50% Ni content yields a batch completion time of 80 minutes while a standard catalyst with 95% Ni content yields a batch time of 75 minutes, the Ni-based productivity ratio for the experimental vs. standard is:

$$\frac{75 \times 95}{80 \times 50} = 1.78$$

That is, the experimental catalyst is much more efficient (i.e., 1.78 times better) on the basis of Ni employed, although its absolute batch time is slightly longer.

Surface area measurements recited in the Examples were measured by BET nitrogen adsorption method. BET uses an adsorption model and related equation to calculate surface area from adsorbed volumes of nitrogen at chosen partial pressures. A particular application of BET surface area measurement is described in S. R. Schmidt, "Surfaces of Raney® Catalysts" in Catalysis of Organic Reactions, eds. M. G. Scaros and M. L. Prunier, pub. Marcel Dekker, 1995.

Bulk chemical analysis of the compositions prepared in the Examples was analyzed by Inductive Coupled Plasma-Atomic Emission Spectroscopy ("ICP"). Each sample was washed with water and then completely dissolved in a mixture of $HCl/NHO_3$ acid (3:1) solution prior to analysis.

Amounts of metals indicated in compositions of the finished catalysts recited in the Examples are on a metals only basis. The sum of the analyzed metals was normalized to 100%, i.e. amounts of non-metal elements, e.g., oxygen, carbon and hydrogen, were not included. In cases where the stated metal percentages total to slightly less than 100%, the unstated remainder of the metal composition consists of unintended trace contaminants.

Example 1

An Fe and Ni containing sponge support was prepared as following:

An alloy was made by mixing 60 parts (by weight) of Al, 27 parts of Fe, 11 parts of Ni and 2 parts of Mo, and then melting them by heating to a maximum temperature of 1550° C., which was maintained for 20 minutes. The melt was poured onto a graphite-cooling slab where it hardened within a few minutes to about 0.5-0.75" thickness.

Subsequently, the alloy slab was broken into smaller pieces and reduced in size to <¼" pieces with a jaw crusher. The crushed material was then ground to a powder using a hammer mill (Micropul). The median diameter of the powdered alloy thus obtained was 31 microns.

Three Hundred (300) g of this powder was added gradually with stirring to a 25% aqueous solution of NaOH (486 g solid NaOH dissolved in 1458 g water). The peak temperature during this alloy addition stage (48 minutes duration) was 90° C. This temperature was maintained by externally applied heating of the agitated slurry of digesting alloy/catalyst for another 3 hours.

After agitation and heating were stopped and the catalyst support was allowed to settle, the byproduct solution of sodium aluminate was removed by decantation. The catalyst support was then washed by decantation method (1. add water, 2. stir, 3. settle, 4. decant) for several times using ~45° C. water, stopping when the pH of the spent wash water was 9.0.

Example 2

A Ni plated sponge catalyst was prepared using the sponge support as prepared as described in Example 1 above. An aqueous slurry containing forty (40) grams of the Fe—Ni sponge prepared in Example 1 in 500 ml of water was placed in a glass vessel fitted with a stirrer and external heating mantle. A Ni containing solution was then made by dissolving 35.1 g of Ni sulfate hydrate (FW 262.8), an amount sufficient to provide a Ni content equivalent of 8 g or 20% Ni relative to the original support weight) in 500 ml water. This solution was then added to the aqueous slurry in the glass mixing vessel and the mixture was stirred for 10 minutes.

A mixture of two reducing agents (34 g Na formate, FW 68, and 53 g $NaH_2PO_2.H_2O$, FW 106) was dissolved in 400 ml water). The pH of this solution was then adjusted to 5.5 by addition of 3M acetic acid. The adjusted solution was then added to the aqueous slurry and the mixture was stirred for 5 minutes. The pH of the mixture was then further adjusted to 5.0 with acetic acid and mixed for 5 additional minutes.

Next the pH of the aqueous slurry was adjusted upward to 5.5 by addition of 10% NaOH solution and the mixture was heated to 70° C. Stirring was continued for 30 minutes at this temperature to complete the first plating step.

Agitation was then discontinued and the catalyst was allowed to settle. The plating solution was removed by decantation and the catalyst was washed twice with 2 L of 45° C. water.

The above steps starting with the addition of the Ni sulfate were repeated except that the amount of Ni sulfate used was 26.2 g (an amount sufficient to provide 15% Ni relative to initial support weight). The washing steps after this second plating used (a) 2 L of 5% NaOH solution at 45° C., (b) 2 L of 5% NaOH solution at room temperature, and (c) repeated 2 L portions of water at 45° C. until a pH of 10.5 was reached.

The surface of the Ni-plated catalyst was promoted with Molybdenum by adding 0.88 g of ammonium heptamolybdate (FW 1235.9) dissolved in 50 ml of water, and then stirring for 30 minutes. Final washing was done with water at 45° C. to reach a pH of 9.5.

The composition of the resulting catalyst was 49.7% Fe, 44.8% Ni, 3.4% Al and 2.0% Mo.

Example 3

A Ni plated sponge catalyst was prepared as described in Example 2 except that the temperature in the plating steps was 85° C. The composition of the resulting catalyst was 49.6% Fe, 44.6% Ni, 3.8% Al and 2.0% Mo.

Example 4

A Ni plated sponge catalyst was prepared as described in Example 2 except the temperature in the plating steps was 50° C. The composition of the resulting catalyst was 51.0% Fe, 43.8% Ni, 3.2% Al and 2.0% Mo.

Example 5

A Ni plated sponge catalyst was prepared as described in Example 2 except that the amount of nickel sulfate used in the two successive plating steps was sufficient to provide 20% Ni each time for an overall nominal Ni plating loading of 40%. The composition of the resulting catalyst was 50.4% Fe, 44.4% Ni, 3.3% Al and 1.9% Mo.

Example 6

A Ni plated sponge catalyst was prepared as described in Example 2 except that the amount of nickel sulfate used Ni loading in the two successive plating steps was reduced to an amount sufficient to provide 15% Ni each time for an overall nominal Ni plating loading of 30%. The composition of the resulting catalyst was 55.0% Fe, 39.4% Ni, 3.6% Al and 2.0% Mo.

Example 7

A Ni plated sponge catalyst was prepared as described in Example 2 except that only the 53 g of $NaH_2PO_2$ was employed as reducing agent in each plating step, omitting Na formate. The composition of the resulting catalyst was 52.3% Fe, 42.1% Ni, 3.6% Al and 1.9% Mo.

Example 8

A Ni plated sponge catalyst was prepared as described in Example 3 except that a sponge support having a Ni content of 12.9%, a Mo content of 1.7% Mo and an Fe content of 77.8% was used. The composition of the resulting plated catalyst was 57.2% Fe, 35.1% Ni, 5.7% Al and 1.8% Mo.

Example 9

A Ni plated sponge catalyst was prepared as described in Example 3 except that a sponge support having a lower Ni content of 12.5%, and an Fe content of 77.7%, but no Mo was used. The composition of the resulting plated catalyst was 53.5% Fe, 38.4% Ni, 7.2% Al and 0.8% Mo.

Example 10

A Ni plated sponge catalyst was prepared as described in Example 2 except that the reducing agent in each plating step was 68 g of Na formate (2× that of Example 3) and omitting Na hypophosphite. The resulting catalyst had a composition of 47.8% Ni, 37.6% Fe, 10.1% Al and 4.3% Mo.

Example 11

A cobalt plated sponge catalyst was prepared as described in Example 2 except that a sponge support having a lower Ni content of 12.5%, and an Fe content of 77.7%, but no Mo was used, and cobalt sulfate (FW 281.1) at 37.5 g and 28.2 g, respectively, in the plating steps was used instead of Ni sulfate. The composition of the resulting catalyst was 31.0% Co, 52.8% Fe, 9.1% Ni, 6.3% Al, and 0.8% Mo. The catalyst had a BET surface area of 62 $m^2/g$.

Example 12

A Cu-based sponge support was made from an alloy with a composition of 48% Cu, 2% Cr, and 50% Al by leaching Al at 90° C. in 25% NaOH solution for 1 hour. The sponge support had a composition of 90.8% Cu, 4.9% Al, 3.4% Cr and 0.6% Ni, and a BET SA of 46 $m^2$ g. The sponge support was plated with Ni using the nickel sulfate amounts of Example 6, but at 85° C. The resulting catalyst had a composition of 73.0% Cu, 4.1% Al, 2.9% Cr, 18.6% Ni, and 0.4% Mo, a BET SA of 50 $m^2/g$. and an XPS Ni/Cu ratio of 3.8.

Example 13

A Ni plated sponge catalyst was prepared as described in Example 7 except that a chelating agent, 40 g of citric acid, was used in the plating solutions instead of acetic acid, and the pH for the plating steps was adjusted to 5.5 with dilute NaOH solution. The resulting catalyst had a composition of 3.6% Al, 43.3% Fe, 5.9% Mo and 47.2% Ni. The measured BET SA was 84 $m^2/g$.

The analyzed metals remaining in solution after plating were 0.33% Fe and 0.39% Ni for the first plating a 0.29% Fe, 0.36% Ni for the second plating. These levels of dissolved Fe and undeposited Ni are much higher than normally observed (levels of less than about 0.06% each were typically observed in Examples 2-10), due to the effect of the optional chelating agent.

Example 14

A cobalt-plated nickel sponge catalyst was prepared as described in Example 11 using a Raney® Ni, Grade 6800, obtained from Grace Davison, Chattanooga, Tenn. The resulting catalyst had a composition of 14.4 Co, 3.2% Al, 81.4% Ni, and 0.6% Mo, a BET surface area of 50 $m^2/g$, and an XPS Co/Ni ratio of 3.8.

Example 15

Testing for the baseline of performance in converting dextrose to sorbitol using Mo/Ni sponge catalyst as the standard was conducted as follows:

Raney® Ni grade R-3111 was obtained from Grace Davison, Chattanooga, Tenn. A catalyst loading of 6.6 weight percent was used, relative to the dextrose (weight of dry solid equivalent) contained in the reaction mixture. This equated to an actual catalyst weight of 12.3 g and an apparent (underwater) catalyst weight of 10.5 g. The underwater weight was determined by comparing the weight of a fixed volume of slurry (catalyst plus water) to the weight of the same volume of water alone. The weight difference was then multiplied by a density-based correction factor of 1.17 to yield actual catalyst weight. The reaction mixture was 272 g of a 68% dextrose (dry solid equivalent) feedstock combined with an additional 228 g of water to make an overall 37% solids solution. The feedstock had approximately a 97% dextrose equivalent or DE assay on a dry basis, and was obtained from Arancia-CPC of Guadalajara, Mexico.

The 37% solution was heated to about 80° C. and stirred to homogeneity, then combined with the catalyst which had been previously weighed under water and charged to the empty 1-L autoclave reactor as an approximately 50% slurry.

The autoclave was sealed, purged of air using nitrogen 3× (pressurized to 100 psig, then released, and then purged 3× and filled with hydrogen (99.999% purity, Air Products) by displacing the nitrogen 3×. Hydrogen was then delivered from a reservoir (pressure bomb) at an initial pressure of about 1000 psig through a pressure regulator to maintain an operating pressure in the reactor of 700 psig throughout the run. The temperature was raised to 140° C. by externally applied electrical resistive heating. The agitation speed was 1900 RPM.

The batch time was monitored starting from when an internal thermocouple indicated the operating temperature had been reached (t=0). Samples (~2 mL) of reaction mixture were removed periodically (at t=60', 70', etc.) by opening a valve, which allowed liquid to be forced through a sintered metal type filter within the reactor and then out through a steel tube to an external sample vial. The reaction was typically allowed to continue beyond the time expected for completion, with subsequent quantifying of completeness of reaction, and efficiency in reaching this endpoint, described as follows.

After a reaction mixture sample was cooled to ambient temperature it was analyzed for residual dextrose content by a Biolyzer unit (from Kodak, now available from Johnson and Johnson Ortho Clinical Diagnostics), which uses a calorimetric end point determined with dry chemical slides to quantify dextrose (glucose) content. This method had previously been calibrated to indicate an endpoint corresponding to conversion of 99.7% of the dextrose originally present. The time at which the endpoint was reached was recorded as the batch time for the catalyst being tested.

Testing: (1-a) The Raney 3111 catalyst thus tested yielded a first-cycle batch time of 75 minutes. This is the standard baseline for productivity calculations in testing at these conditions.

In this and the subsequent Examples, in the event that a catalyst was 'recycled' for testing of its durability (retention of productivity), the catalyst contained in the reactor was allowed to settle after cooling, stopping agitation, and depressurizing the reactor system. Then the sorbitol product was removed by pumping it away without disturbing the settled catalyst.

A new solution of dextrose in water was then added to the reactor and the test procedure was repeated as described above. This method may be repeated an arbitrary number of 'cycles' (batch tests). A catalyst's batch time for a given cycle may be compared both to the $1^{st}$ cycle batch time for the same catalyst (to indicate rate of deactivation or loss of by the catalyst) and to the corresponding cycle's batch time for another catalyst (for ranking absolute batch times at equal catalyst age).

Testing: (1-b) Re-testing of the std. R 3111 performed at a lower catalyst loading of 7.6 g apparent weight (8.9 g true weight) equivalent to 4.8 weight percent loading vs. dextrose solids. The catalyst was recycled 3 times for a total of 4 test cycles. The batch completion times were 75, 75, 85 and 95 minutes. This equates to cycle time ratios (vs. first, shortest cycle) of 1.00, 1.07 and 1.27 for cycles 2-4.

Testing: (1-c) Re-testing of the std. R 3111 performed again at a catalyst loading of 10.3 g apparent weight (12.0 g true weight), but with 50% dextrose solution, equivalent to 4.8 weight percent loading vs. dextrose solids. The catalyst was recycled 2 times for a total of 3 test cycles. The batch completion times were 80 minutes for all three cycles. This equates to cycle time ratios (vs. first, shortest cycle) of 1.00 and 1.00 for cycles 2-3.

Example 16

Ni plated sponge catalysts as prepared in Examples 1-10 were tested for sorbitol production using procedures of Testing (1-a), (1-b) and (1-c) as described in Example 14. Results are recorded in Table 1 below.

TABLE 1

Raney ® Ni and Ni-Plated Catalyst Testing Results

| Example | % Dextrose | Cat. Loading (wt %) | Batch Completion Times (min) | | | Cycle 1 Productivity Ratio | Cycle 1 Prod. Ratio vs. % Ni |
| --- | --- | --- | --- | --- | --- | --- | --- |
| | | | Cycle 1 | Cycle 2 | Cycle 3 | | |
| 15 (1a) | 37 | 6.6 | 75 | | | 1 (std) | 1 (std) |
| 15 (1b) | 37 | 4.8 | 75 | 75 | 85 | 1 (std) | 1 (std) |
| 15 (1c) | 50 | 4.8 | 80 | 80 | 80 | 1 (std) | 1 (std) |
| 2 | 37 | 6.6 | 80 | 80 | | 0.94 | 2.0 |
| 2 | 37 | 4.8 | 80 | 85 | 95 | 0.94 | 2.0 |
| 2 | 50 | 4.8 | 80 | 80 | 80 | 1.00 | 2.1 |
| 3 | 37 | 4.8 | 75 | | | 1.00 | 2.1 |
| 4 | 37 | 4.8 | 85 | 85 | | 0.88 | 1.9 |
| 5 | 37 | 4.8 | 80 | 120 | | 0.94 | 2.0 |
| 6 | 37 | 4.8 | 80 | | | 0.94 | 2.3 |
| 7 | 37 | 4.8 | 80 | | | 0.94 | 2.1 |
| 8 | 37 | 4.8 | 90 | | | 0.83 | 2.2 |
| 9 | 37 | 4.8 | 80 | | | 0.94 | 2.3 |
| 10 | 37 | 4.8 | 80 | | | 0.94 | 1.9 |

Comparative Example 1

For comparative purposes, sponge catalysts A, B and C having reduced amounts of Ni and increased amounts of Fe as compared to conventional Raney Ni catalyst were prepared using the alloys as described below. No deposition of Ni was performed on the finished sponge catalyst. The finished catalysts were tested to determine productivity for converting dextrose to sorbitol.

Catalyst A: An alloy containing 50% Al, 27.5% Ni, 5% Mo and 17.5% Fe was made and then activated as described in Example 1. The resulting sponge catalyst had a Ni content of 52%. The catalyst was tested at the conditions of Example 15(b). The Ni/Fe atomic ratio of the catalyst was determined by XPS. Results are recorded in Table 2 below.

Catalyst B: An alloy containing 50% Al, 21.3% Ni, 7.5% Mo and 21.2% Fe was made and then activated as described in Example 1. The resulting sponge catalyst had a Ni content of 42%. The catalyst was tested at the conditions of Example 15(b). The Ni/Fe atomic ratio of the catalyst was determined by XPS. Results are recorded in Table 2 below.

Catalyst C: An alloy containing 50% Al, 17.5% Ni, 5% Mo and 27.5% Fe was made and then activated as described in Example 1. The resulting sponge catalyst had a Ni content of 35%. The catalyst was tested as described in Example 15(b). The Ni/Fe atomic ratio of the catalyst was determined by XPS. Results are recorded in Table 2 below.

Comparative Example 2

For comparison purposes, various sponge supports were tested to determine productivity for converting dextrose to sorbitol without deposition of Ni on the surface of the support. A sponge support containing (A) 24% Ni, as employed in Examples 2-7, and a support containing (B) 13% Ni, as employed in Example 8, were tested for one cycle each at the conditions of Example 15(b), yielding, respectively, batch completion times of 110 and >>120 minutes (incomplete at 120 minutes). These equate to productivity ratios of 0.68 and <<0.63, respectively. The catalyst was characterized for Ni/Fe atomic ratio by XPS. Results are recorded in Table 2 below.

Comparative Example 3

For comparison purposes, a Ni plated sponge catalyst was prepared using a chemical reducing agent but at high pH. The sponge support employed had a Ni content of 23.4%, 58.7% Fe and 2.8% Mo. The plating was accomplished using a 1-hour duration at 60° C., and as plating solution reagents the equivalent of 20% Ni (relative to support weight) in the form of $NiCl_2 \cdot 6H_2O$, a 1.85:1 weight ratio of $Na_4EDTA$ to support, and 0.42:1 weight ratio of $NaH_2PO_2$—$H_2O$ to support. Analyses before and after the plating process showed no significant deposition of Ni under these conditions. Testing as described in Example 15(b) failed to complete the batch conversion even after 150 minutes. Productivity results and Ni/Fe atomic ratios are recorded in Table 2 below.

TABLE 2

| Example No. | Ni Content (%) | Batch Time (min) | Productivity Ratio | XPS Ni/Fe |
|---|---|---|---|---|
| Comparative 1A | 52 | 105 | 0.71 | 0.22 |
| Comparative 1B | 42 | 120 | 0.62 | 0.12 |
| Comparative 1C | 35 | 140 | 0.54 | 0.16 |
| Comparative 2A | 24 | 110 | 0.68 | 0.01–0.03 |
| Comparative 2B | 13 | >>120 | <<0.63 | NA |
| Comparative 3 | 49 | >150 | <0.5 | |
| 3 | 45 | 75 | 1.0 | |
| 6 | 39 | 80 | 0.94 | 0.54 |
| 9 | 38 | 80 | 0.94 | |

As shown in Table 2, catalysts prepared in Comparative Example 1 from precursor alloys containing Ni and having no Ni plating exhibited a lower catalyst performance when compared to the performance of catalysts of the invention in Examples 3, 6 and 9. The lower catalyst performance was also evident in Comparative Example 2 where the precursor alloys had an increased Fe concentration and a reduced Ni concentration.

Table 2 also showed that the Ni plated sponge catalyst of Comparative Example 3, prepared by a plating process that employed a high pH with a chemical reducing agent, had a low catalyst performance when compared to catalysts prepared in accordance with the process of the present invention.

Comparative Example 4

For comparison purposes, a Ni plated catalyst was prepared as described in Example 4, with the exception that the pH during the plating was 5.8 and no reducing agent was added. The resulting catalyst had a Ni content of 48.7%, 44.1% Fe, 4.5% Al and 2.6% Mo. The resulting catalyst was tested as described in Example 15(b). Testing failed to complete the batch conversion even after 150 minutes.

I claim:

1. A method of preparing a nickel and/or cobalt plated sponge catalyst comprising
    (a) preparing an aqueous slurry containing a sponge support having surface area;
    (b) adding to the aqueous slurry a salt of a metal selected from the group consisting of nickel, cobalt and mixture thereof, in an amount sufficient to deposit a catalytically effective amount of the metal on at least a portion of the surface area of the sponge support and to form a plating slurry containing ions of metal;
    (c) adding a reducing agent to the plating slurry in an amount sufficient to reduce the metal ions in the slurry to the corresponding metal;
    (d) adjusting the pH and temperature of the plating slurry in a manner sufficient to deposit the metal on the surface of the support and form a metal coated sponge catalyst; and,
    (e) removing the catalyst from the plating slurry.

2. The method of claim 1 wherein the metal salt is selected from the group consisting of sulfates, chlorides, nitrates, acetates, citrates, and mixtures thereof.

3. The method of claim 1 wherein the concentration of sponge support in the aqueous slurry of step (a) ranges from about 2 to about 15 weight percent of the slurry.

4. The method of claim 3 wherein the concentration of sponge support in the aqueous slurry ranges from about 3 to about 12 weight percent of the slurry.

5. The method of claim 4 wherein the concentration of sponge support in the aqueous slurry ranges from about 5 to about 10 weight percent of the slurry.

6. The method of claim 1 wherein the concentration of metal salt added to the slurry is a concentration sufficient to provide at least 10 weight percent of metal relative to the weight of the support.

7. The method of claim 6 wherein the concentration of metal salt added to the slurry is a concentration sufficient to provide greater than 15 weight percent of metal relative to the weight of the support.

8. The method of claim 1 further comprising adjusting the pH of the aqueous slurry to range from about 5 to about 6 prior to addition of the metal salt.

9. The method of claim 1 wherein the reducing agent is selected from the group consisting of salts of formic acid, salts of carboxylic acids other than formic acid, carboxylic acids, low molecular weight aldehydes, sugars, hypophosphite, borohydride, aminoboranes, lithium aluminum hydride, hydrazine, low molecular weight alcohols, and mixtures thereof.

10. The method of claim 9 wherein the reducing agent is selected from the group consisting of formaldehyde, sodium hypophosphite, sodium formate, gluconate, oxalate, sodium borohydride and mixtures thereof.

11. The method of claim 1 wherein the reducing agent is added to the plating slurry in an amount sufficient to reduce substantially all of the nickel and/or cobalt ions in the slurry to the corresponding metal.

12. The method of claim 1 wherein the reducing agent is added to the plating slurry in a stoichiometric amount sufficient to achieve the redox reaction with the metal ions in the slurry.

13. The method of claim 1 further comprising adding a chelating agent to the plating slurry.

14. The method of claim 1 further comprising adding a stabilizer to the plating slurry.

15. The method of claim 14 wherein the stabilizer is a metal selected from the group consisting of chromium, titanium, niobium, tantalum, zirconium, vanadium, molybdenum, manganese, tungsten, bismuth, and mixtures thereof.

16. The method claim 1 wherein the sponge support is maintained under a non-oxidizing atmosphere during steps (a)-(e) of the method.

17. The method of claim 1 wherein in step (d) the pH of the plating slurry is adjusted to a pH of at least about 5.5 and the temperature of the plating slurry is adjusted to at least 30° C.

18. The method of claim 1 further comprising initiating the deposition of nickel and/or cobalt on the support by electrochemical displacement prior to step (d).

19. The method of claim 18 wherein the deposition of nickel and/or cobalt is initiated by adjusting the pH of the plating slurry to about 5 and maintaining the pH for a time sufficient to initiate electrochemical displacement of support metal by nickel and/or cobalt from the plating slurry.

20. The method of claim 1 wherein steps (a)-(e) are repeated to apply multiple coatings of nickel and/or cobalt on the support.

21. The method of claim 1 further comprising step (f), which is washing the catalyst for a time and at a temperature sufficient to neutralize or remove substantially all residues and salts.

22. The method of claim 1 or 21 further comprising depositing a metal promoter on the surface of the catalyst.

23. The method of claim 22 wherein the metal promoter is a metal selected from the group consisting of chromium, molybdenum, titanium, zinc, vanadium, zirconium and mixtures thereof.

24. The method of claim 23 wherein the metal promoter is in a zero valent state.

25. The method of claim 23 wherein the metal promoter is in an oxidized form.

26. The method of claim 21 further comprising depositing a precious metal dopant on the surface of the catalyst.

27. The method of claim 26 wherein the precious metal dopant is a metal or a compound of a metal selected from the group consisting platinum, palladium, iridium, rhodium, osmium, ruthenium, rhenium and mixtures thereof.

28. A method of preparing a nickel and/or cobalt coated sponge catalyst, which comprises (a) a metal sponge support having a surface and comprising (1) about 2 to about 40 weight percent of a metal selected from the group consisting of nickel, cobalt and mixture thereof, and (2) at least one metal which is different from the metal(s) coated on the metal sponge support, and (b) a metal selected from the group consisting of nickel, cobalt, and mixture thereof, coated on at least a portion of the surface of the metal sponge support, the method comprising:

(a) preparing an aqueous slurry containing a metal sponge support having surface area, and comprising (1) about 2 to about 40 weight percent of a metal selected from the group consisting of nickel, cobalt and mixture thereof, and (2) at least one metal which is different from the metal(s) coated on the metal sponge support;

(b) adding to the aqueous slurry a salt of a metal selected from the group consisting of nickel, cobalt and mixture thereof, in an amount sufficient to deposit a catalytically effective amount of the metal on at least a portion of the surface area of the metal sponge support and to form a plating slurry containing ions of metal;

(c) adding a reducing agent to the plating slurry in an amount sufficient to reduce the metal ions in the slurry to the corresponding metal;

(d) adjusting the pH and temperature of the plating slurry in a manner sufficient to deposit the metal on the surface of the support and form the nickel and/or cobalt coated metal sponge catalyst; and, (e) removing the nickel and/or cobalt coated metal sponge catalyst from the plating slurry.

29. The method of claim 28 wherein in step (d) the pH of the plating slurry is adjusted to a pH of at least about 5.5 and the temperature of the plating slurry is adjusted to at least 30° C.

30. The method of claim 28 further comprising initiating the deposition of nickel and/or cobalt on the support by electrochemical displacement prior to step (d).

31. The method of claim 28 wherein steps (a)-(e) are repeated to apply multiple coatings of nickel and/or cobalt on the support.

32. The method of claim 28 further comprising step (f), which is washing the catalyst for a time and at a temperature sufficient to neutralize or remove substantially all residues and salts.

33. The method of claim 28 further comprising depositing a metal promoter on the surface of the catalyst.

34. The method of claim 32 further comprising depositing a metal promoter on the surface of the catalyst.

35. The method of claim 28 further comprising depositing a precious metal dopant on the surface of the catalyst.

* * * * *